United States Patent
Hauck et al.

(10) Patent No.: US 9,782,130 B2
(45) Date of Patent: Oct. 10, 2017

(54) ROBOTIC SURGICAL SYSTEM (75) Inventors: John A. Hauck, Shoreview, MN (US); Jeffrey A. Schweitzer, St. Paul, MN (US); Troy T. Tegg, Elk River, MN (US); James D. Essington, Brooklyn Park, MN (US); Mark T. Johnson, Mounds View, MN (US); Kedar Ravindra Belhe, Minnetonka, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 3469 days.

(21) Appl. No.: 11/647,300

(22) Filed: Dec. 29, 2006

(65) Prior Publication Data
US 2007/0185486 A1 Aug. 9, 2007

Related U.S. Application Data (63) Continuation-in-part of application No. 11/139,908, filed on May 27, 2005, now Pat. No. 7,632,265.
(Continued)

(51) Int. Cl.
*A61B 18/18* (2006.01)
*A61B 5/00* (2006.01)
(Continued)

(52) U.S. Cl.
CPC ............ *A61B 5/6885* (2013.01); *A61B 34/20* (2016.02); *A61B 34/70* (2016.02); *A61B 34/71* (2016.02);
(Continued)

(58) Field of Classification Search
CPC ....... A61B 5/6885; A61B 34/20; A61B 34/30; A61B 34/71; A61B 34/70;
(Continued)

(56) References Cited

U.S. PATENT DOCUMENTS 4,510,574 A 4/1985 Giottet et al.
4,710,876 A 12/1987 Cline et al.
(Continued)

FOREIGN PATENT DOCUMENTS

EP 1779802 5/2007
WO WO 97/44089 11/1997
(Continued)

OTHER PUBLICATIONS

International Search Report for PCT Application No. PCT/US07/080702 filed Oct. 8, 2007 and Written Opinion dated Apr. 16, 2008.
(Continued)

*Primary Examiner* — David Shay
(74) *Attorney, Agent, or Firm* — Wiley Rein LLP (57) ABSTRACT A robotic surgical system includes a track, a catheter holding device including a catheter receiving portion translatably associated with the track, a translation servo mechanism to control translation of the catheter holding device relative to the track, a catheter deflection control mechanism, a deflection servo mechanism to control the catheter deflection control mechanism, and a controller to control at least one of the servo mechanisms. The catheter receiving portion is adapted for quick installation and removal of a catheter. The catheter receiving portion may be rotatable, with a rotation servo mechanism to control the rotatable catheter receiving portion. The controller controls at least one of the deflection and rotation servo mechanisms to maintain a substantially constant catheter deflection as the catheter rotates. An introducer, which may be steerable, and an expandable, collapsible sterile tube may also be provided.

2 Claims, 9 Drawing Sheets

Related U.S. Application Data (60) Provisional application No. 60/851,042, filed on Oct. 12, 2006, provisional application No. 60/575,741, filed on May 28, 2004.

(51) Int. Cl.
*A61B 34/20* (2016.01)
*A61B 17/00* (2006.01)
*A61M 25/01* (2006.01)
*A61B 34/00* (2016.01)
*A61B 90/00* (2016.01)
*A61B 34/30* (2016.01)

(52) U.S. Cl.
CPC ..... *A61B 34/30* (2016.02); *A61B 2017/00026* (2013.01); *A61B 2034/2051* (2016.02); *A61B 2034/301* (2016.02); *A61B 2034/742* (2016.02); *A61B 2090/064* (2016.02); *A61B 2090/3784* (2016.02); *A61M 25/0105* (2013.01)

(58) Field of Classification Search
CPC .... A61B 2017/00026; A61B 2034/742; A61B 2034/301; A61B 2034/205; A61B 2090/064; A61B 2090/3784; A61M 25/0105
USPC .......................... 606/1; 604/95.05, 158; 901/2
See application file for complete search history.

(56) References Cited

U.S. PATENT DOCUMENTS

| | | |
|---|---|---|
| 4,721,114 A | 1/1988 | DuFault et al. |
| 4,785,399 A | 11/1988 | Evans et al. |
| 4,837,734 A | 6/1989 | Ichikawa et al. |
| 4,854,324 A | 8/1989 | Hirschman et al. |
| 4,873,572 A | 10/1989 | Miyazaki et al. |
| 4,921,482 A | 5/1990 | Hammerslag et al. |
| 5,078,140 A | 1/1992 | Kwoh |
| 5,114,414 A | 5/1992 | Buchbinder |
| 5,199,950 A | 4/1993 | Schmitt et al. |
| 5,222,501 A | 6/1993 | Ideker et al. |
| RE34,502 E | 1/1994 | Webster, Jr. |
| 5,275,164 A | 1/1994 | Maeda et al. |
| 5,281,220 A | 1/1994 | Blake |
| 5,339,799 A | 8/1994 | Kami et al. |
| 5,368,564 A | 11/1994 | Savage |
| 5,385,148 A | 1/1995 | Lesh et al. |
| 5,389,073 A | 2/1995 | Imran |
| 5,391,147 A | 2/1995 | Imran et al. |
| 5,391,199 A | 2/1995 | Ben-Haim |
| 5,396,887 A | 3/1995 | Imran |
| 5,400,783 A | 3/1995 | Pomeranz et al. |
| 5,404,638 A | 4/1995 | Imran |
| 5,406,946 A | 4/1995 | Imran |
| 5,409,000 A | 4/1995 | Imran |
| 5,415,166 A | 5/1995 | Imran |
| 5,423,811 A | 6/1995 | Imran et al. |
| 5,425,364 A | 6/1995 | Imran |
| 5,425,375 A | 6/1995 | Chin et al. |
| 5,431,645 A | 7/1995 | Smith et al. |
| 5,465,717 A | 11/1995 | Imran et al. |
| 5,476,100 A | 12/1995 | Galel |
| 5,478,330 A | 12/1995 | Imran et al. |
| 5,492,131 A | 2/1996 | Galel |
| 5,496,311 A | 3/1996 | Abele et al. |
| 5,498,239 A | 3/1996 | Galel et al. |
| 5,507,802 A | 4/1996 | Imran |
| 5,527,279 A | 6/1996 | Imran |
| 5,533,967 A | 7/1996 | Imran |
| 5,545,161 A | 8/1996 | Imran |
| 5,555,897 A * | 9/1996 | Lathrop et al. .................. 5/600 |
| 5,558,073 A | 9/1996 | Pomeranz et al. |
| 5,578,007 A | 11/1996 | Imran |
| 5,588,964 A | 12/1996 | Imran et al. |
| 5,607,462 A | 3/1997 | Imran |
| 5,632,734 A | 5/1997 | Galel et al. |
| 5,656,029 A | 8/1997 | Imran et al. |
| 5,658,278 A | 8/1997 | Imran et al. |
| 5,662,108 A | 9/1997 | Budd et al. |
| 5,673,704 A | 10/1997 | Marchlinski et al. |
| 5,680,860 A | 10/1997 | Imran |
| 5,681,280 A | 10/1997 | Rusk et al. |
| 5,697,377 A | 12/1997 | Wittkampf |
| 5,697,927 A | 12/1997 | Imran et al. |
| 5,722,401 A | 3/1998 | Pietroski et al. |
| 5,730,128 A | 3/1998 | Pomeranz et al. |
| 5,754,741 A | 5/1998 | Wang et al. |
| 5,782,899 A | 7/1998 | Imran |
| RE35,880 E | 8/1998 | Waldman et al. |
| 5,800,482 A | 9/1998 | Pomeranz et al. |
| 5,808,665 A | 9/1998 | Green |
| 5,813,991 A | 9/1998 | Willis et al. |
| 5,820,568 A | 10/1998 | Willis |
| 5,823,199 A | 10/1998 | Hastings et al. |
| 5,835,458 A | 11/1998 | Bischel et al. |
| 5,861,024 A | 1/1999 | Rashidi |
| 5,876,325 A | 3/1999 | Mizuno et al. |
| 5,882,333 A | 3/1999 | Schaer et al. |
| 5,882,346 A | 3/1999 | Pomeranz et al. |
| 5,895,417 A | 4/1999 | Pomeranz et al. |
| 5,906,605 A | 5/1999 | Coxum |
| 5,908,446 A | 6/1999 | Imran |
| 5,940,240 A | 8/1999 | Kupferman |
| 5,954,665 A | 9/1999 | Ben-Haim |
| 5,964,732 A | 10/1999 | Willard |
| 5,964,796 A | 10/1999 | Imran |
| 5,971,967 A | 10/1999 | Willard |
| 5,983,126 A | 11/1999 | Wittkampf |
| 5,993,462 A | 11/1999 | Pomeranz et al. |
| 5,997,532 A | 12/1999 | McLaughlin et al. |
| 6,004,271 A | 12/1999 | Moore |
| 6,010,500 A | 1/2000 | Sherman et al. |
| 6,014,579 A | 1/2000 | Pomeranz et al. |
| 6,015,407 A | 1/2000 | Rieb et al. |
| 6,032,077 A | 2/2000 | Pomeranz |
| 6,049,732 A | 4/2000 | Panescu et al. |
| 6,063,022 A | 5/2000 | Ben-Haim |
| 6,066,125 A | 5/2000 | Webster |
| 6,075,871 A | 6/2000 | Simanovsky et al. |
| 6,083,170 A | 7/2000 | Ben-Haim |
| 6,089,235 A | 7/2000 | Hastings et al. |
| 6,096,004 A | 8/2000 | Meglan et al. |
| 6,119,041 A | 9/2000 | Pomeranz et al. |
| 6,123,699 A | 9/2000 | Webster |
| 6,197,017 B1 | 3/2001 | Brock et al. |
| 6,210,362 B1 | 4/2001 | Ponzi |
| 6,216,027 B1 | 4/2001 | Willis et al. |
| 6,221,060 B1 | 4/2001 | Willard |
| 6,227,077 B1 | 5/2001 | Chiang |
| 6,235,022 B1 | 5/2001 | Hallock et al. |
| 6,236,883 B1 | 5/2001 | Ciaccio et al. |
| 6,241,666 B1 | 6/2001 | Pomeranz et al. |
| 6,258,060 B1 | 7/2001 | Willard |
| 6,272,371 B1 | 8/2001 | Shlomo |
| 6,285,898 B1 | 9/2001 | Ben-Haim |
| 6,289,239 B1 | 9/2001 | Panescu et al. |
| 6,292,681 B1 | 9/2001 | Moore |
| 6,298,257 B1 | 10/2001 | Hall et al. |
| 6,375,471 B1 | 4/2002 | Wendlandt et al. |
| 6,398,755 B1 | 6/2002 | Belef et al. |
| 6,432,112 B2 | 8/2002 | Brock et al. |
| 6,436,107 B1 | 8/2002 | Wang et al. |
| 6,451,027 B1 | 9/2002 | Cooper et al. |
| 6,490,474 B1 | 12/2002 | Willis et al. |
| 6,493,608 B1 | 12/2002 | Niemeyer |
| 6,500,167 B1 | 12/2002 | Webster |
| 6,516,211 B1 | 2/2003 | Acker et al. |
| 6,517,477 B1 | 2/2003 | Wendlandt |
| 6,554,820 B1 | 4/2003 | Wendlandt et al. |
| 6,554,844 B2 | 4/2003 | Lee et al. |
| 6,569,160 B1 | 5/2003 | Goldin et al. |
| 6,572,554 B2 | 6/2003 | Yock |

(56) References Cited

U.S. PATENT DOCUMENTS

| | | |
|---|---|---|
| 6,596,084 B1 | 7/2003 | Patke |
| 6,620,202 B2 | 9/2003 | Bottcher et al. |
| 6,640,119 B1 | 10/2003 | Budd et al. |
| 6,650,920 B2 | 11/2003 | Schaldach et al. |
| 6,659,956 B2 | 12/2003 | Barzell et al. |
| 6,663,622 B1 | 12/2003 | Foley et al. |
| 6,679,269 B2 | 1/2004 | Swanson |
| 6,679,836 B2 | 1/2004 | Couvillon |
| 6,692,485 B1 | 2/2004 | Brock et al. |
| 6,695,785 B2 | 2/2004 | Brisken et al. |
| 6,699,179 B2 | 3/2004 | Wendlandt |
| 6,716,190 B1 | 4/2004 | Glines et al. |
| 6,718,196 B1 | 4/2004 | Mah et al. |
| 6,719,804 B2 | 4/2004 | St. Pierre |
| 6,726,675 B1 | 4/2004 | Beyar |
| 6,728,562 B1 | 4/2004 | Budd et al. |
| 6,731,976 B2 | 5/2004 | Penn et al. |
| 6,752,800 B1 | 6/2004 | Winston et al. |
| 6,764,450 B2 | 7/2004 | Yock |
| 6,770,027 B2 | 8/2004 | Bunik et al. |
| 6,783,521 B2 | 8/2004 | Ponzi et al. |
| 6,810,281 B2 | 10/2004 | Brock et al. |
| 6,817,974 B2 | 11/2004 | Cooper et al. |
| 6,835,173 B2 | 12/2004 | Couvillon et al. |
| 6,837,867 B2 | 1/2005 | Kortelling |
| 6,843,793 B2 | 1/2005 | Brock et al. |
| 6,858,003 B2 | 2/2005 | Evans et al. |
| 6,860,878 B2 | 3/2005 | Brock |
| 6,872,178 B2 | 3/2005 | Weinberg |
| 6,874,789 B2 | 4/2005 | Shedlov |
| 6,892,091 B1 | 5/2005 | Ben-Haim et al. |
| 6,913,594 B2 | 7/2005 | Coleman et al. |
| 6,926,669 B1 | 8/2005 | Stewart et al. |
| 6,939,309 B1 | 9/2005 | Beatty et al. |
| 6,946,092 B1 | 9/2005 | Bertolino et al. |
| 6,947,785 B1 | 9/2005 | Beatty et al. |
| 6,949,106 B2 | 9/2005 | Brock et al. |
| 6,955,674 B2 | 10/2005 | Eick et al. |
| 6,962,669 B2 | 11/2005 | Foreman et al. |
| 6,974,455 B2 | 12/2005 | Garabedian et al. |
| 6,974,465 B2 | 12/2005 | Belef et al. |
| 6,978,168 B2 | 12/2005 | Beatty et al. |
| 6,990,370 B1 | 1/2006 | Beatty et al. |
| 6,997,870 B2 | 2/2006 | Couvillon |
| 7,022,077 B2 | 4/2006 | Mourad et al. |
| 7,025,064 B2 | 4/2006 | Wang et al. |
| 7,027,892 B2 | 4/2006 | Wang et al. |
| 7,037,345 B2 | 5/2006 | Bottcher et al. |
| 7,076,300 B1 | 7/2006 | Kroll et al. |
| 7,189,208 B1 | 3/2007 | Beatty et al. |
| 7,344,533 B2 | 3/2008 | Pearson |
| 7,466,303 B2 * | 12/2008 | Yi et al. ............ 606/1 |
| 7,479,106 B2 | 1/2009 | Banik |
| 7,632,265 B2 | 12/2009 | Hauck et al. |
| 7,806,829 B2 | 10/2010 | Hauck |
| 2001/0027316 A1 | 10/2001 | Gregory |
| 2002/0042570 A1 | 4/2002 | Schaldach et al. |
| 2002/0045810 A1 | 4/2002 | Ben-Haim |
| 2002/0087166 A1 | 7/2002 | Brock et al. |
| 2002/0087169 A1 | 7/2002 | Brock et al. |
| 2002/0123749 A1 | 9/2002 | Jain |
| 2002/0128633 A1 | 9/2002 | Brock et al. |
| 2002/0143319 A1 | 10/2002 | Brock |
| 2002/0143326 A1 | 10/2002 | Foley et al. |
| 2002/0177789 A1 | 11/2002 | Ferry et al. |
| 2003/0036696 A1 | 2/2003 | Willis |
| 2003/0055410 A1 | 3/2003 | Evans |
| 2003/0199904 A1 | 10/2003 | Boecker et al. |
| 2004/0049205 A1 | 3/2004 | Lee et al. |
| 2004/0059237 A1 | 3/2004 | Narayan et al. |
| 2004/0073206 A1 | 4/2004 | Foley et al. |
| 2004/0098075 A1 | 5/2004 | Lee |
| 2004/0128026 A1 | 7/2004 | Harris et al. |
| 2004/0176751 A1 | 9/2004 | Weitzner et al. |
| 2004/0193146 A1 | 9/2004 | Lee et al. |
| 2005/0004579 A1 | 1/2005 | Sneider et al. |
| 2005/0049580 A1 | 3/2005 | Brock et al. |
| 2005/0096643 A1 | 5/2005 | Brucker et al. |
| 2005/0102017 A1 | 5/2005 | Mattison |
| 2005/0137478 A1 | 6/2005 | Younge et al. |
| 2005/0192488 A1 | 9/2005 | Bryenton et al. |
| 2005/0197530 A1 | 9/2005 | Wallace et al. |
| 2005/0203382 A1 | 9/2005 | Govari et al. |
| 2005/0203394 A1 | 9/2005 | Hauck |
| 2005/0215983 A1 | 9/2005 | Brock |
| 2005/0216033 A1 | 9/2005 | Lee et al. |
| 2005/0222554 A1 * | 10/2005 | Wallace et al. ............ 606/1 |
| 2005/0228440 A1 | 10/2005 | Brock et al. |
| 2005/0234437 A1 | 10/2005 | Baxter et al. |
| 2006/0004352 A1 | 1/2006 | Vaska et al. |
| 2006/0015096 A1 | 1/2006 | Hauck et al. |
| 2006/0052695 A1 | 3/2006 | Adam |
| 2006/0057560 A1 | 3/2006 | Hlavkak et al. |
| 2006/0058692 A1 | 3/2006 | Beatty et al. |
| 2006/0084945 A1 | 4/2006 | Moll et al. |
| 2006/0084960 A1 | 4/2006 | Mester et al. |
| 2006/0095022 A1 | 5/2006 | Moll et al. |
| 2006/0098010 A1 | 5/2006 | Dwyer |
| 2006/0100610 A1 | 5/2006 | Wallace et al. |
| 2006/0111692 A1 | 5/2006 | Moll et al. |
| 2006/0116575 A1 | 6/2006 | Willis |
| 2006/0149139 A1 | 7/2006 | Bonmassar et al. |
| 2006/0258935 A1 | 11/2006 | Pile-Spellman et al. |
| 2007/0021679 A1 | 1/2007 | Narayan et al. |
| 2007/0043296 A1 | 2/2007 | Schwartz |
| 2007/0057945 A1 | 3/2007 | Olson |
| 2007/0060833 A1 | 3/2007 | Hauck |
| 2007/0073179 A1 | 3/2007 | Afonso et al. |
| 2007/0185485 A1 | 8/2007 | Hauck et al. |
| 2007/0197896 A1 | 8/2007 | Moll et al. |
| 2007/0208260 A1 | 9/2007 | Afonso |
| 2008/0015670 A1 | 1/2008 | Pappone |
| 2009/0105579 A1 | 4/2009 | Garibaldi |

FOREIGN PATENT DOCUMENTS

| | | |
|---|---|---|
| WO | WO 00/07503 | 2/2000 |
| WO | WO0007501 | 2/2000 |
| WO | WO0125822 | 4/2001 |
| WO | WO-2004/047632 | 6/2004 |
| WO | 2005042053 | 5/2005 |
| WO | 2005044081 | 5/2005 |
| WO | WO-2005/042053 | 5/2005 |
| WO | WO2005112750 | 5/2005 |
| WO | WO 2005/117596 A2 | 12/2005 |
| WO | 2007005976 | 1/2007 |
| WO | 2006059089 A1 | 6/2009 |

OTHER PUBLICATIONS

International Search Report for PCT Application No. PCT/US07/080706 filed Oct. 8, 2007 and Written Opinion dated Jun. 23, 2008.

International Search Report for PCT Application No. PCT/US07/080705 filed Oct. 8, 2007 and Written Opinion dated Apr. 16, 2008.

International Search Report for PCT Application No. PCT/US07/080701 filed Oct. 8, 2007 and Written Opinion dated Apr. 15, 2008.

International Search Report for PCT Application No. PCT/US07/080703 filed Oct. 8, 2007 and Written Opinion dated Apr. 16, 2008.

International Search Report for International Application No. PCT/US2007/080698, filed Oct. 8, 2007, with Written Opinion of the International Searching Authority dated May 13, 2008.

International Search Report for International Application No. PCT/US2008/073694 Filed Aug. 20, 2008, and Written Opinion dated Nov. 13, 2008.

"Supplementary European Search Report", EP 08798257 Aug. 17, 2011.

Extended European Search Report issued in Application No. EP 08 79 8257, dated Aug. 17, 2011.

* cited by examiner

FIG.9

ROBOTIC SURGICAL SYSTEM

CROSS-REFERENCE TO RELATED APPLICATIONS

This application claims the benefit of U.S. provisional application No. 60/851,042, filed 12 Oct. 2006, which is hereby expressly incorporated by reference as though fully set forth herein.

This application is a continuation-in-part of U.S. application Ser. No. 11/139,908, filed 27 May 2005 (the '908 application), now pending, which claims the benefit of U.S. provisional application No. 60/575,741, filed 28 May 2004 (the '741 application). The '908 and '741 applications are hereby expressly incorporated by reference as though fully set forth herein.

BACKGROUND OF THE INVENTION a. Field of the Invention

The instant invention relates to robotically controlled medical devices. In particular, the instant invention relates to a robotic surgical system for navigating a medical device through a patient's body for diagnostic and therapeutic purposes.

b. Background Art

Catheters are used for an ever growing number of medical procedures. To name just a few examples, catheters are used for diagnostic, therapeutic, and ablation procedures. Typically, the user manually manipulates the catheter through the patient's vasculature to the intended site, such as a site within the patient's heart. The catheter typically carries one or more electrodes or other diagnostic or therapeutic devices, which may be used for ablation, diagnosis, cardiac mapping, or the like.

It is well known that, to facilitate manipulation of the catheter through the patient's vasculature to the intended site, portions of the catheter shaft, especially the distal regions thereof, may be made steerable. For example, the catheter may be manufactured such that the user can translate, rotate, and deflect the distal end of the catheter as necessary and desired to negotiate the tortuous paths of the patient's vasculature en route to the target site. Navigating a catheter reliably through the patient's body to a precise location, however, is an extremely tedious process requiring a substantial amount of time and skill and potentially causing a high degree of fatigue in the physician, especially where actuation forces are transmitted over large distances.

BRIEF SUMMARY OF THE INVENTION

It is thus desirable to be able to navigate a medical device accurately and precisely through a patient's body to the locations of diagnostic or therapeutic interest.

It is also desirable to be able to reduce the fatigue factor associated with navigating a medical device through a patient's body.

It is further desirable to be able to preserve the ability to manually navigate a medical device when so desired.

According to a first aspect of the invention, a robotic surgical system includes: a track; a catheter holding device translatably associated with the track and including a catheter receiving portion; a translation servo mechanism operatively coupled to the catheter holding device and adapted to control translation of the catheter holding device relative to the track; a catheter deflection control mechanism; a deflection servo mechanism operatively coupled to and adapted to control the catheter deflection control mechanism; and a controller operatively coupled to and adapted to control at least one of the translation and deflection servo mechanisms. Preferably, the catheter receiving portion is adapted for quick installation and removal of a catheter. Optionally, the catheter holding device includes the catheter deflection control mechanism.

The catheter holding device may be slideable relative to the track or may be translatably associated with the track via a screw mechanism such as a worm gear, a lead screw, or a ball screw. Preferably, the catheter holding device can translate relative to the track a total distance of about 10 cm. The catheter holding device itself may be mounted on the track. Alternatively, a carriage may be translatably mounted on the track, with the catheter holding device mounted on the carriage such that the catheter holding device translates relative to the track with the carriage. Optionally, either or both of the catheter deflection control mechanism and the deflection servo mechanism may be mounted on the carriage.

In some embodiments of the invention, the catheter receiving portion is rotatable, preferably by at least about 360°, with a rotation servo mechanism operatively coupled to and adapted to control the rotatable catheter receiving portion. The rotation servo mechanism may also be carriage-mounted. Further, the controller may be operatively coupled to both the rotation servo mechanism and the deflection servo mechanism and adapted to control at least one of, and optionally both, the rotation servo mechanism and the deflection servo mechanism to maintain a substantially constant catheter deflection as the catheter receiving portion rotates.

A catheter having a distal end and a proximal end, a catheter control handle near the proximal end, and at least one pull wire extending from the catheter control handle to the distal end may be received in the catheter receiving portion such that it translates relative to the track with the catheter holding device, thereby providing a first degree of freedom to the catheter. In addition, the catheter may be operatively coupled to the catheter deflection control mechanism such that actuation of the catheter deflection control mechanism causes the distal end of the catheter to deflect, thereby providing a second degree of freedom to the catheter. The catheter control handle may include a catheter deflection actuator operatively coupled to the catheter deflection control mechanism to selectively tension at least one pull wire, and optionally at least four pull wires. In embodiments with a rotating catheter receiving portion, the catheter may rotate with the catheter receiving portion, thereby providing a third degree of freedom to the catheter.

To provide a substantially sterile field about the catheter outside the patient's body, an expandable, collapsible tube may surround at least a portion of the catheter. The expandable, collapsible tube may be constructed of a plurality of telescoping tubular elements.

An introducer, which extends into a patient such that a distal end of the introducer is proximate a target site, may also be provided as part of the robotic surgical system. A proximal end of the introducer may be stationary, while the distal end may be steerable via a robotic control system including at least one servo mechanism adapted to control the distal end of the introducer in at least one degree of freedom. Optionally, the robotic control system for the introducer includes three servo mechanisms adapted to control the distal end of the introducer in three degrees of freedom.

In another embodiment of the invention, a robotic surgical system includes: a track; a carriage mounted on the track; a translation servo mechanism operatively coupled to the carriage and adapted to control movement of the carriage relative to the track; a catheter holding device including a catheter deflection mechanism and a rotatable catheter receiving portion, wherein the catheter holding device is mounted on the carriage such that the catheter holding device moves relative to the track with the carriage; a rotation servo mechanism operatively coupled to the catheter holding device and adapted to control rotation of the catheter receiving portion; a deflection servo mechanism operatively coupled to the catheter deflection mechanism and adapted to control deflection of a catheter that may be received in the catheter receiving portion; a controller coupled to at least the rotation servo mechanism and the deflection servo mechanism, wherein the controller simultaneously controls the deflection servo mechanism and the rotation servo mechanism to maintain a substantially constant catheter deflection during rotation of the catheter receiving portion; an introducer designed to extend into a patient such that a distal end of the introducer is proximate a target site; and a telescoping tube for creating a sterile field between the catheter holding device and a proximal end of the introducer. A catheter received in the catheter receiving portion translates relative to the track with the catheter holding device and rotates about its axis as the catheter receiving portion rotates. The catheter is operatively coupled to the catheter deflection mechanism such that actuation of the catheter deflection mechanism causes a distal end of the catheter to deflect.

According to yet another aspect of the invention, a method of manufacturing a surgical system includes the steps of: translatably associating a catheter holding device including a rotatable catheter holding device with a track; operatively coupling a translation servo mechanism to the catheter holding device to control translation of the catheter holding device relative to the track; operatively coupling a rotation servo mechanism to the catheter holding device for controlling rotation of the catheter receiving portion about its axis; providing a catheter deflection control mechanism; operatively coupling a deflection servo mechanism to the catheter deflection control mechanism to control the catheter deflection control mechanism; and coupling a controller to at least the deflection servo mechanism and the rotation servo mechanism, wherein the controller controls at least one of the deflection servo mechanism and the rotation servo mechanism in order to maintain a substantially constant catheter deflection as the catheter receiving portion rotates. Optionally, the controller simultaneously controls both the deflection servo mechanism and the rotation servo mechanism.

In still another aspect of the invention, a method of controlling a catheter to treat tissue includes the steps of: providing a robotic catheter control system including a translatable catheter holding device including a catheter receiving portion, a translation mechanism adapted to control translation of the catheter holding device, a deflection mechanism adapted to control deflection of the catheter, and a robotic controller operatively coupled to and adapted to control the translation mechanism and the deflection mechanism; receiving the catheter in the catheter receiving portion such that the catheter translates with the catheter holding device; operatively coupling the catheter to the deflection mechanism such that actuation of the deflection control mechanism causes deflection of the catheter; and robotically navigating the catheter to one or more locations within a patient by actuating one or more of the translation mechanism and the deflection mechanism. Optionally, the method further includes operatively coupling a rotation mechanism to the catheter receiving portion to control rotation thereof, wherein robotically navigating the catheter may also include actuating the rotation mechanism. The deflection mechanism may be actuated to maintain a substantially constant deflection of the catheter distal end during rotation of the catheter.

Also disclosed is a robotic surgical system to control a first medical device in at least two degrees of freedom and a second medical device in at least two degrees of freedom. The robotic surgical system includes: a first holding device adapted to receive the first medical device therein; a second holding device adapted to receive the second medical device therein; a first robotic control system, including at least two servo mechanisms, that is operatively coupled to the first holding device and adapted to control the first medical device in at least two degrees of freedom; a second robotic control system, including at least two servo mechanisms, that is operatively coupled to the second holding device and adapted to control the second medical device in at least two degrees of freedom; and at least one controller operatively coupled to said first robotic control system and said second robotic control system to cooperatively control the first and second medical devices in at least two degrees of freedom each.

A method of calibrating a robotically controlled catheter is also disclosed. The method includes the following steps: providing a robotic control input to the catheter to deflect the distal end of the catheter; measuring a deflection of the distal end of the catheter; associating the measured deflection of the distal end of the catheter with the robotic control input; and generating a calibration data set, the calibration data set comprising a plurality of associated measured deflections and robotic control inputs. Typically, the distal end of the catheter will be deflected between a first extreme and a second extreme. In addition, the distal end of the catheter may be advanced beyond a distal end of an introducer, in which instance the calibration data set includes a plurality of associated measured deflections and robotic control inputs for a given advancement of the distal end of the catheter beyond the distal end of the introducer.

An advantage of the present invention is a reduced exposure to radiation for both the patient and the physician, since the present invention reduces the time required to navigate the catheter to a target location and minimizes the need for fluoroscopy to locate the catheter within the patient.

Another advantage of the present invention is the ability to easily switch between automated robotic control and manual control of the catheter.

Still another advantage of the present invention is the ability to remotely interact with the robotic surgical system controlling the catheter.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
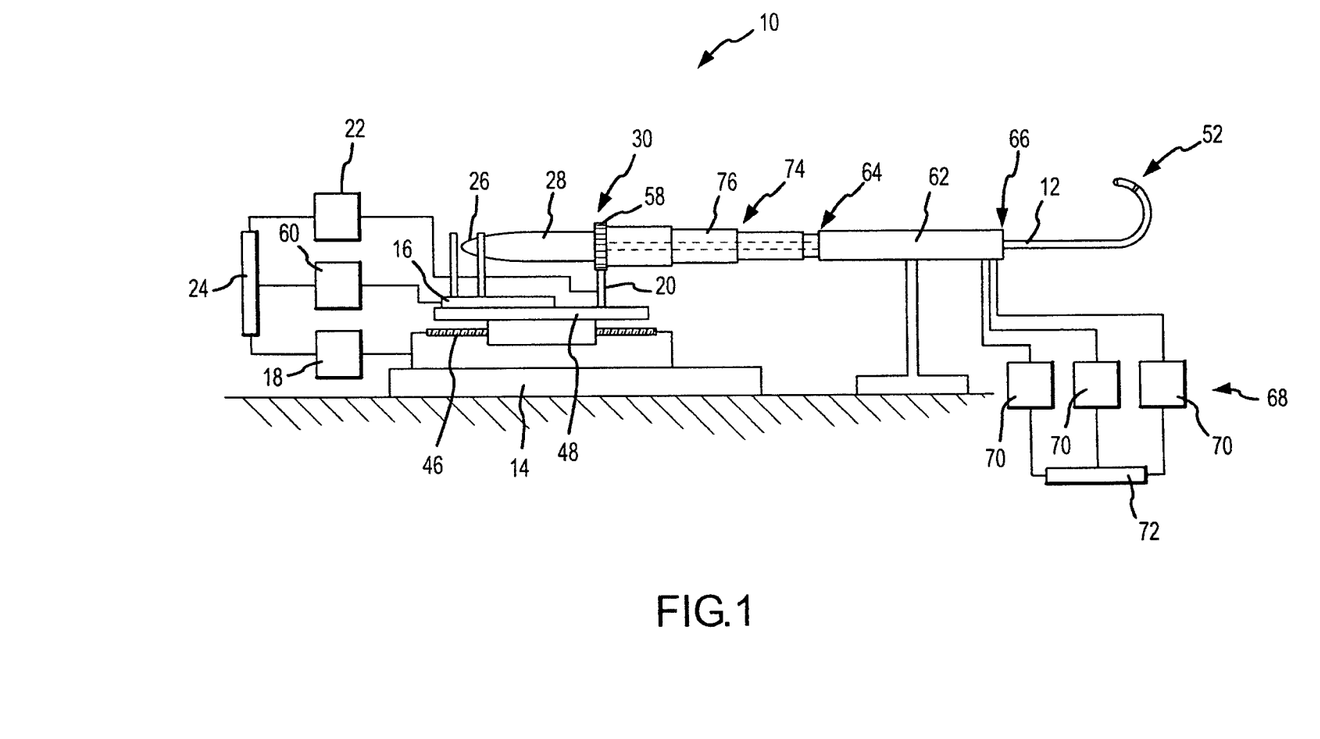
FIG. 1 is a schematic illustration of an embodiment of a robotic surgical system.

FIG. 1 schematically illustrates an embodiment of a robotic surgical system 10 for robotic manipulation and control of a medical device 12. Medical device 12 is preferably a catheter, which may be any type of catheter, including, by way of example only and without limitation, an ablation catheter, a guide wire catheter, an introducer catheter, a probe, or a stylet. It should be understood, however, that any other therapeutic, diagnostic, or assistive medical device may be controlled by robotic surgical system 10 without departing from the scope of the present invention. Such other devices include, but are not limited to, syringes, electrophoresis devices, iontophoresis devices, transdermal pharmaceutical delivery devices, myoblast delivery devices, stem cell delivery devices, ablation devices, stents, and pacemaker leads, which may be carried on or delivered by a catheter. It should further be understood that robotic surgical system 10 may be used to manipulate and control more than one medical device 12 in accordance with the quick installation and removal feature described herein. Accordingly, the terms "medical device," "probe," "therapeutic device," and "catheter" are used interchangeably herein.

Robotic surgical system 10 generally includes a track 14, a catheter holding device 16, a translation servo mechanism 18, a catheter deflection control mechanism 20, a deflection servo mechanism 22, and a controller 24 operatively coupled to at least one of translation servo mechanism 18 and deflection servo mechanism 22. Translation and deflection servo mechanisms 18, 22 may be any type of device for providing mechanical control at a distance, including continuous motors, stepper motors, hydraulic actuators, pulley systems, and other devices known to those of ordinary skill in the art. Catheter deflection control mechanism 20 and deflection servo mechanism 22 are collectively referred to herein as a "catheter deflection mechanism."

Catheter holding device 16 includes a catheter receiving portion 26. Catheter receiving portion 26 is configured to receive catheter 12 by installing a catheter control handle 28, located near a proximal end 30 of catheter 12, into catheter receiving portion 26. Preferably, catheter receiving portion 26 is adapted for quick installation and removal of any type of catheter 12 (or, as noted above, another medical device), thereby facilitating the installation of device 12 for control by robotic surgical system 10 and removal of device 12 for manual control (e.g., user manipulation of catheter control handle 28). Accordingly, catheter control handle 28 may be secured in catheter receiving portion 26 by a frictional fit or with one or more quick-release fasteners. Alternatively, the inner surface of catheter receiving portion 26 and the outer surface of catheter control handle 28 may include mating threaded portions to permit catheter control handle 28 to be screwed into catheter holding device 16. In other embodiments of robotic surgical system 10, catheter control handle 28 is clamped or strapped in place in catheter receiving portion 26. An adapter may also be used to facilitate the reception of catheter control handle 28 within catheter receiving portion 26.

Figure 2:
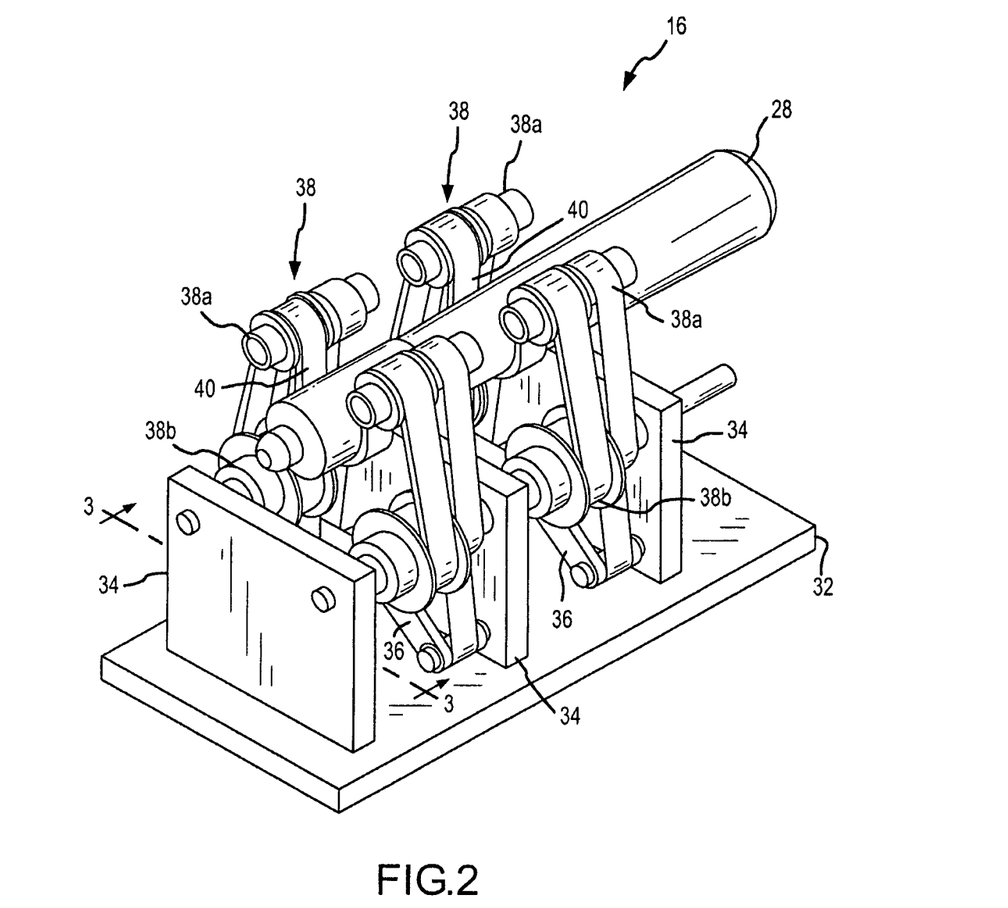
FIG. 2 is a perspective view of one embodiment of a catheter holding device with a catheter placed therein.
Figure 3:
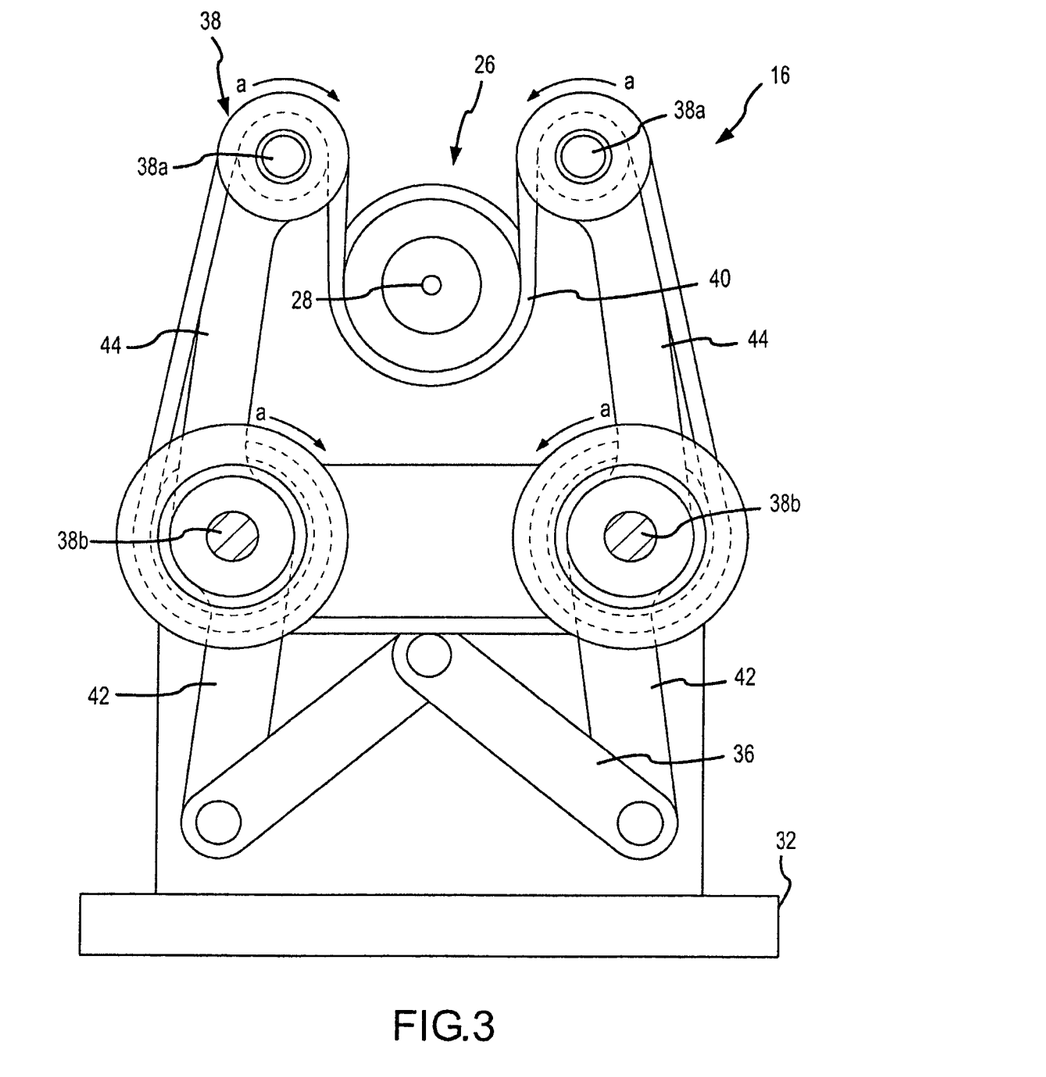
FIG. 3 is an end view of the catheter holding device of FIG. 2.

One embodiment of catheter holding device 16 is illustrated in FIGS. 2 and 3 with catheter control handle 28 placed, but not secured, therein. Catheter holding device 16 includes a base plate 32 and a plurality of upstanding support plates 34. Support plates 34 support cams 36, which are connected to pulley systems 38.

Figure 4:
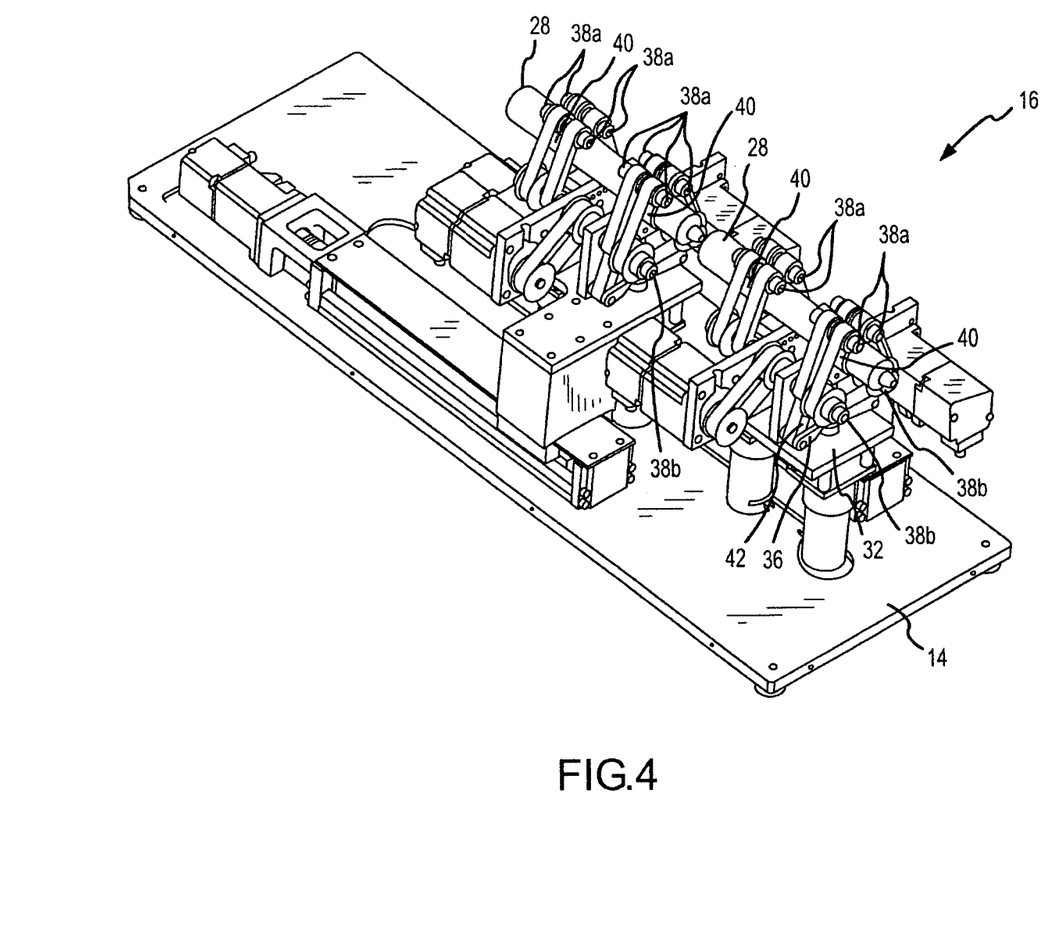
FIG. 4 is a perspective view of one embodiment of a catheter holding device with a catheter secured therein.
Figure 5:
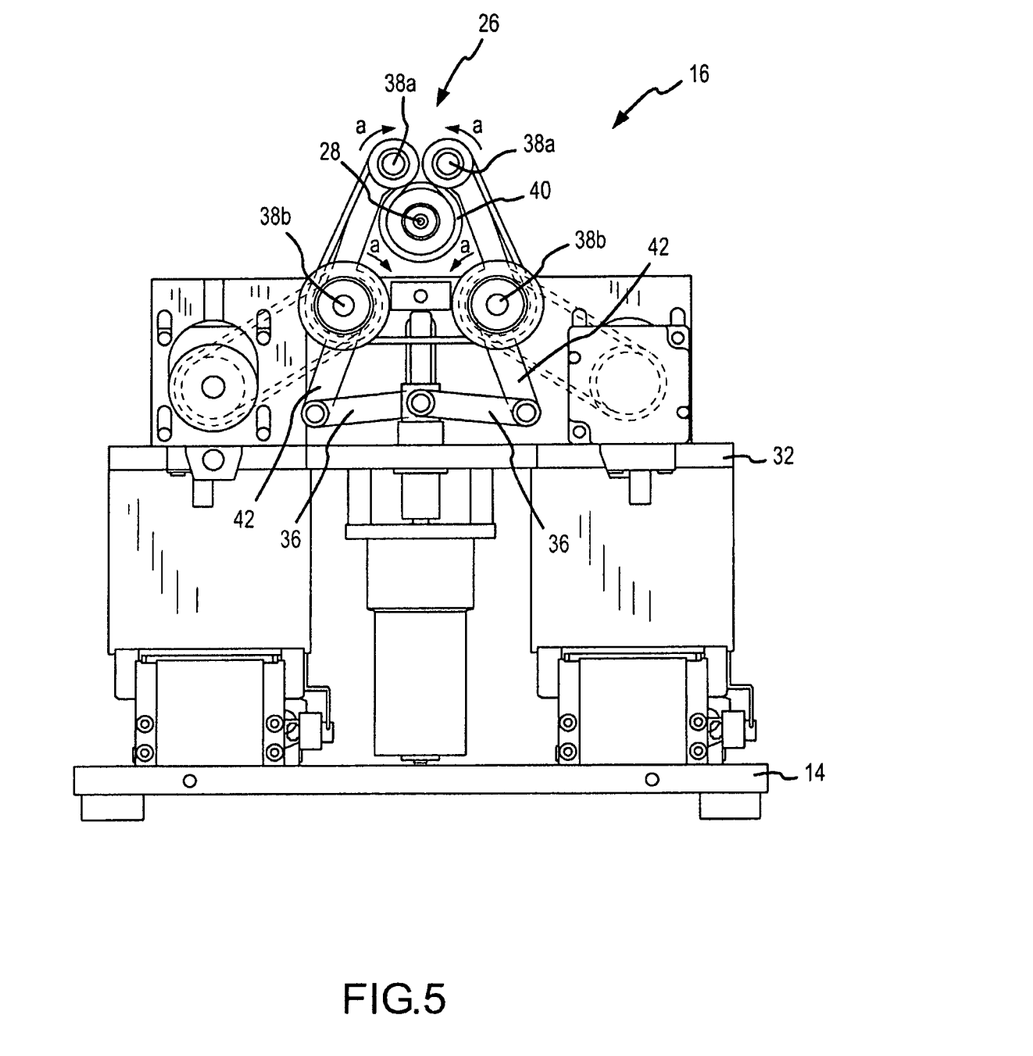
FIG. 5 is an end view of the catheter holding device of FIG. 4.

Catheter control handle 28 is received downwardly through an opening 40 into the catheter receiving portion 26 and onto belts 40 of pulley systems 38. As catheter control handle is urged downwardly, belts 40 rotate upper and lower pulleys 38a, 38b in the direction of arrows a. This, in turn, urges cams 36 downwards via links 42 and draws upper pulleys 38a, 38b towards one another via links 44, while simultaneously wrapping the belts 40 about catheter control handle 28. Catheter control handle 28 is thereby secured within catheter receiving portion 26 as shown in FIGS. 4 and 5. To remove catheter control handle 28 from catheter holding device 16, the user need only release cams 26, which reverses the process described above and opens catheter receiving portion 26.

Catheter holding device 16 is translatably associated with track 14. The phrase "translatably associated with" encompasses all types of relative lateral motion between catheter holding device 16 and track 14. For example, catheter holding device 16 may slide relative to track 14. Alternatively, catheter holding device 16 may move laterally along a screw mechanism 46, such as a worm gear, a lead screw, or a ball screw, attached to track 14. Preferably, catheter holding device 16 has a translation range relative to track 14 (i.e., the lateral distance that catheter holding device 16 can travel relative to track 14 between extremes) of at least about 5 cm, the approximate width of a human heart. More preferably, the translation range of catheter holding device 16 relative to track 14 is at least about 10 cm.

In the preferred embodiment of the invention, a carriage 48 is translatably mounted on track 14 via screw mechanism 46. Catheter holding device 16 is mounted on carriage 48 such that catheter holding device 16 translates relative to track 14 with carriage 48. For example, base plate 32 may be fixedly or removably mounted on carriage 48. Alternatively, catheter holding device 16 may be integrally formed with carriage 48 as a single assembly (i.e., base plate 32 and carriage 48 may be a single, unitary component). Likewise, in some embodiments of the invention, catheter holding device 16 may be translatably mounted directly on track 14 without an intervening carriage.

Translation servo mechanism 18 is operatively coupled to catheter holding device 16 and adapted to control translation of catheter holding device 16 relative to track 14 in order to adjust the lateral position of catheter holding device 16 along track 14. Preferably, translation servo mechanism 18 is operatively coupled to carriage 48 in order to move carriage 48, and therefore catheter holding device 16 mounted thereon, laterally along track 14. In the embodiment shown in FIG. 1, translation servo mechanism 18 drives screw mechanism 46, thereby moving carriage 48 laterally therealong.

Deflection servo mechanism 22 is operatively coupled to and adapted to control catheter deflection control mechanism 20. In the preferred embodiment of the invention, deflection servo mechanism 22 is operatively coupled to catheter deflection control mechanism 20 such that deflection servo mechanism 22 can rotate catheter deflection control mechanism 20. Either or both of deflection servo mechanism 22 and catheter deflection control mechanism 20 may be mounted on carriage 48 in order to simplify the transmission system linking deflection servo mechanism 22 and catheter deflection control mechanism 20. In some embodiments of robotic surgical system 10, catheter deflection control mechanism 20 is incorporated in catheter holding device 16, for example by utilizing pulley systems 38, and in particular belts 40, as further described below. One of ordinary skill in the art will appreciate, however, that catheter deflection control mechanism 20 may also be separated from catheter holding device 16 without departing from the spirit and scope of the present invention.

Controller 24 is adapted to control at least one of translation servo mechanism 18 and deflection servo mechanism 22 in order to navigate catheter 12 received in catheter holding device 16. It should also be noted that the use of multiple controllers to control translation servo mechanism 18 and deflection servo mechanism 22 is regarded as within the scope of the present invention. Throughout this disclosure, the term "controller" refers to a device that controls the movement or actuation of one or more robotic systems (that is, the component responsible for providing command inputs to the servo mechanisms). One of ordinary skill in the art will understand how to select an appropriate controller for any particular mechanism within robotic surgical system 10. Further, the term "controller" should be regarded as encompassing both a singular, integrated controller and a plurality of controllers for actuating one or more robotic systems.

Figure 6:
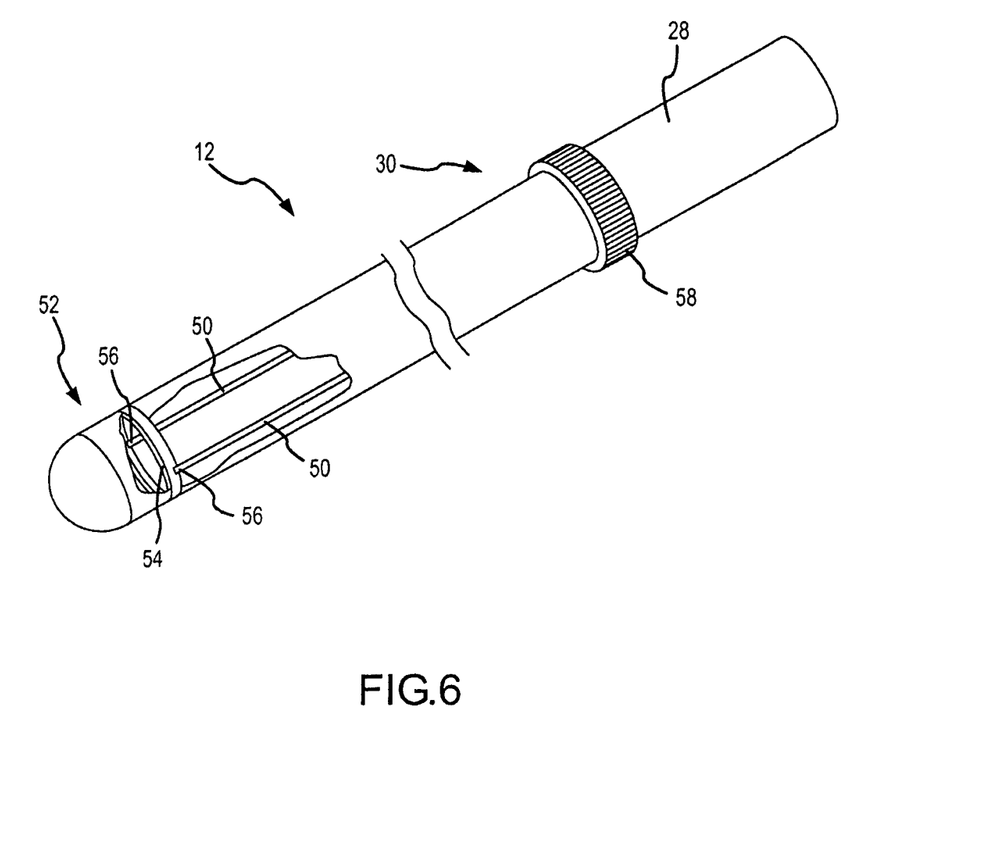
FIG. 6 illustrates an exemplary steerable catheter such as may be used in the robotic surgical system.

As shown in FIG. 6, catheter 12 is preferably a steerable catheter including at least one pull wire 50 extending from catheter control handle 28 near proximal end 30 of catheter 12 to a distal end 52 of catheter 12. Pull wires 50 may be coupled to at least one pull ring 54, also located near distal end 52 of catheter 12. When placed in tension, pull wires 50 deflect distal end 52 of catheter 12 into various configurations. As one of skill in the art will understand, additional pull wires 50 will enhance the deflection versatility of distal end 52 of catheter 12. For example, a single pull wire 50 with a single point of attachment to pull ring 54 will permit distal end 52 of catheter 12 to deflect on a single axis, and perhaps in only one direction, for example upwards relative to FIG. 6. By adding a second pull wire 50 (as shown in FIG. 6), or by looping a single pull wire 50 to have two points of attachment 56 to pull ring 54, distal end 52 of catheter 12 may be deflected in two directions, for example both upwards and downwards relative to FIG. 6. A catheter 12 with four pull wires 50 attached to pull ring 54 at about 90° intervals can deflect in four directions, for example upwards, downwards, and into and out of the plane of the paper relative to FIG. 6.

One or more catheter deflection actuators 58 may be provided on catheter control handle 28 to selectively tension one or more pull wires 50, thereby controlling the direction and degree of deflection of distal end 52 of catheter 12. In some embodiments, one or more knobs may be provided, rotation of which selectively tension one or more pull wires 50. It should be understood, however, that catheter deflection actuators 58 may take many other forms, including, but not limited to, sliders and switches, without departing from the spirit and scope of the present invention. Additionally, it is contemplated that rotating catheter control handle 28 itself may selectively tension pull wires 50 and deflect distal end 52 of catheter 12.

Returning to FIG. 1, when catheter control handle 28 is received within catheter receiving portion 26, catheter 12 translates relative to track 14 with catheter holding device 16, thereby providing a first degree of freedom permitting catheter 12 to be advanced into and retracted from a patient's body. Additionally, catheter 12 is operatively coupled to catheter deflection control mechanism 20 such that actuation of catheter deflection control mechanism 20 causes distal end 52 of catheter 12 to deflect, thereby providing a second degree of freedom to catheter 12. In particular, catheter deflection actuator 58 may be operatively coupled to catheter deflection control mechanism 20 such that catheter deflection control mechanism 20 can actuate catheter deflection actuator 58 to selectively tension one or more pull wires 50 and deflect the distal end 52 of catheter 12 by a desired amount in a desired direction.

In some embodiments of the invention, rotating catheter deflection control mechanism 20 will rotate catheter deflection actuator 58 in turn, thereby selectively tensioning one or more pull wires 50 within catheter 12. The transmission system between catheter deflection control mechanism 20 and catheter deflection actuator 58 may be a frictional fit provided, for example, by rubberized coatings surrounding catheter deflection control mechanism 20 and catheter deflection actuator 58. Alternatively, catheter deflection control mechanism 20 and catheter deflection actuator 58 may be coupled with mating gear teeth or knurling.

Referring specifically to the embodiment of catheter holding device 16 depicted in FIGS. 2-5, when catheter 12 is secured in catheter receiving portion 26, belts 40 frictionally engage catheter control handle 28. They may also engage catheter deflection actuator 58. Thus, if pulley system 38 is driven by deflection servo mechanism 22, belts 40 may rotate catheter control handle 28, catheter deflection actuator 58, or both, in order to selectively tension one or more pull wires 50 and deflect distal end 52 of catheter 12.

It should be understood that the particular configurations of catheter deflection control mechanism 20 and catheter deflection actuator 58 described above are merely exemplary and can be modified without departing from the spirit and scope of the invention. For example, if catheter deflection actuator 58 is a slider rather than a knob, catheter deflection control mechanism 20 may be suitably modified, or even replaced as a modular unit, to actuate a slider. This facilitates the quick connect/disconnect operation of robotic surgical system 10 by allowing easy installation and interconnection between off-the-shelf medical devices of varying construction and robotic surgical system 10.

As described above, the inclusion of additional pull wires 50 in catheter 12 increases the number of directions in which distal end 52 of catheter 12 can deflect. This is referred to herein as "deflection versatility." Where relatively few pull wires 50 (e.g., fewer than about four pull wires 50) are used, however, compensation for lost deflection versatility may be had by rotating catheter 12 about its axis. For example, in a catheter using only a single pull wire 50 with a single point of attachment to pull ring 54, permitting the catheter to deflect only in one direction, the catheter may be deflected in the opposite direction simply by rotating it 180° about its axis. Similarly, a catheter that can deflect in two directions 180° apart can be deflected in the directions midway therebetween by rotating the catheter 90° about its axis.

Accordingly, in some embodiments of the invention, catheter receiving portion 26 is rotatable. An example of such a rotatable catheter receiving portion is catheter receiving portion 26 defined by pulley system 38 depicted in FIGS. 2-5. A rotation servo mechanism 60 is operatively coupled to rotatable catheter receiving portion 26 and adapted to control rotatable catheter receiving portion 26. Thus, pulley system 38 may be driven by rotation servo mechanism 60, thereby engaging belts 40 to rotate catheter 12 about its axis.

If desired, rotation servo mechanism 60 may be mounted on carriage 48 or affixed to catheter holding device 16 such that rotation servo mechanism 60 translates relative to track 14 with catheter holding device 16. This arrangement creates a fixed-distance relationship between rotation servo mechanism 60 and catheter holding device 16, which can simplify the transmission system coupling rotation servo mechanism 60 to catheter holding device 16.

When installed in catheter holding device 16, catheter 12 rotates with catheter receiving portion 26, thereby providing a third degree of freedom to catheter 12 and compensating for low deflection versatility attributable to a relatively lower number of pull wires 50. Catheter receiving portion 26 is preferably rotatable at least about 360° about its axis, such that catheter 12 received therein is also rotatable at least about 360° about its axis, thereby facilitating deflection of distal end 52 of catheter 12 in substantially any direction, significantly enhancing the deflection versatility of the distal end 52 of the catheter 12. Catheter receiving portion 26 may also be designed to rotate about 720° or more about its axis.

Rotating catheter 12 by rotating catheter receiving portion 26 may cause inadvertent deflection of distal end 52 of catheter 12. As one skilled in the art will recognize from this disclosure, as catheter receiving portion 26 and catheter 12 rotate, catheter deflection actuator 58 may remain stationary, rather than rotating with catheter control handle 28, if the torque applied by rotation servo mechanism 60 is insufficient to overcome the inertia of catheter deflection control mechanism 20. That is, catheter deflection actuator 58 may bind against catheter deflection control mechanism 20, causing relative rotation between catheter control handle 28 and catheter deflection actuator 58. This relative rotation may result in uncommanded tensioning of one or more pull wires 50, inadvertently deflecting distal end 52 of catheter 12.

To maintain a substantially constant deflection as catheter 12 rotates, therefore, controller 24 may be operatively coupled to both rotation servo mechanism 60 and deflection servo mechanism 22. Controller 24 is adapted to control at least one of deflection servo mechanism 22 and rotation servo mechanism 60, and preferably to simultaneously control both deflection servo mechanism 22 and rotation servo mechanism 60, to maintain a substantially constant deflection of distal end 52 as catheter receiving portion 26 and catheter 12 rotate. For example, as controller 24 commands rotation servo mechanism 60 to rotate catheter receiving portion 26, controller 24 may simultaneously command deflection servo mechanism 22 to actuate catheter deflection control mechanism 20 to counter-rotate, thereby substantially eliminating relative rotation between the catheter deflection actuator 58 and catheter control handle 28, helping to maintain a substantially constant deflection of catheter 12. Alternatively, as controller 24 commands rotation servo mechanism 60 to rotate catheter receiving portion 26, it may simultaneously command deflection servo mechanism 22 to decouple catheter deflection control mechanism 20 from catheter deflection actuator 58, thereby permitting catheter deflection actuator 58 to rotate freely with catheter control handle 28. In either case, controller 24 may be configured to eliminate the need to couple deflection servo mechanism 22 and rotation servo mechanism 60 through a mechanical transmission system such as a differential. Further, though described herein as a single controller adapted to control the translation, deflection, and rotation servo mechanisms 18, 22, 60, multiple controllers may be used without departing from the spirit and scope of the present invention.

An introducer 62, preferably a steerable introducer, and most preferably an Agilis™ steerable introducer, may be provided as part of robotic surgical system 10. A proximal end 64 of introducer 62 is preferably stationary, while a distal end 66 of introducer 62 extends into a patient (not shown for clarity) to a location proximate a target site (the term "target" is used herein to refer to a location at which treatment or diagnosis occurs). Introducer 62 may be steerable via a robotic control system 68 including at least one servo mechanism 70 adapted to control distal end 66 of introducer 62 in at least one degree of freedom. Preferably, robotic control system 68 includes three servo mechanisms 70 adapted to control distal end 66 of the introducer 62 in three degrees of freedom (translation, deflection, and rotation), resulting in a total of six degrees of freedom for robotic surgical system 10, and at least one controller 72 adapted to control servo mechanisms 70. Similar control principles may be applied to steerable introducer 62 as are described herein with respect to robotic surgical system 10 and medical device 12.

One of ordinary skill in the art will appreciate that the deflection of distal end 52 of catheter 12 is a function not only of the input to catheter deflection actuator 58 (i.e., the selective tensioning of one or more pull wires 50), but also of the extent to which catheter 12 is advanced beyond a generally rigid sheath, such as introducer 62. That is, the further distal end 52 of catheter 12 is advanced beyond distal end 66 of introducer 62, the greater the deflection of distal end 52 of catheter 12 will be for a given input at catheter deflection actuator 58.

It is therefore desirable to calibrate the deflection of distal end 52 of catheter 12 in terms of both catheter deflection control mechanism inputs and extensions of catheter 12 beyond distal end 66 of introducer 62. By robotically actuating catheter deflection control mechanism 20 between extremes (e.g., commanding a complete rotation of catheter deflection actuator 58) and measuring the resulting deflection of distal end 52 of catheter 12 (e.g., using a localization system), catheter deflection control mechanism inputs may be correlated with deflections of distal end 52 for a given extension of catheter 12 beyond distal end 66 of introducer 62. A similar process may be performed for a multiple different extensions of catheter 12 beyond distal end 66 of introducer 62, resulting in a family of calibration curves relating catheter deflection control mechanism inputs to deflections of distal end 52 of catheter 12. Each curve corresponds to a particular extension of catheter 12 beyond distal end 66 of introducer 62; the amount of extension of catheter 12 beyond distal end 66 of introducer 62 may be derived, at least in part, from the amount of translation of catheter holding device 16 relative to track 14.

To create a substantially sterile field around catheter 12 outside the patient's body, an expandable and collapsible tubular shaft 74 substantially surrounds at least a portion of catheter 12, such as the region of catheter 12 between catheter holding device 16 and proximal end 64 of introducer 62. Preferably, shaft 74 is sterilized before use along with other relevant components of robotic surgical system 10. As catheter holding device 16 translates to advance catheter 12 into the patient (i.e., to the right in FIG. 1), tubular shaft 74 collapses upon itself. Contrarily, as catheter holding device 16 translates to retract catheter 12 from the patient (i.e., to the left in FIG. 1), tubular shaft 74 expands. Preferably, tubular shaft 74 is assembled from a plurality of telescoping tubular elements 76. It is contemplated, however, that tubular shaft 74 may alternatively be an accordion-pleated or other expandable and collapsible structure.

Figure 7:
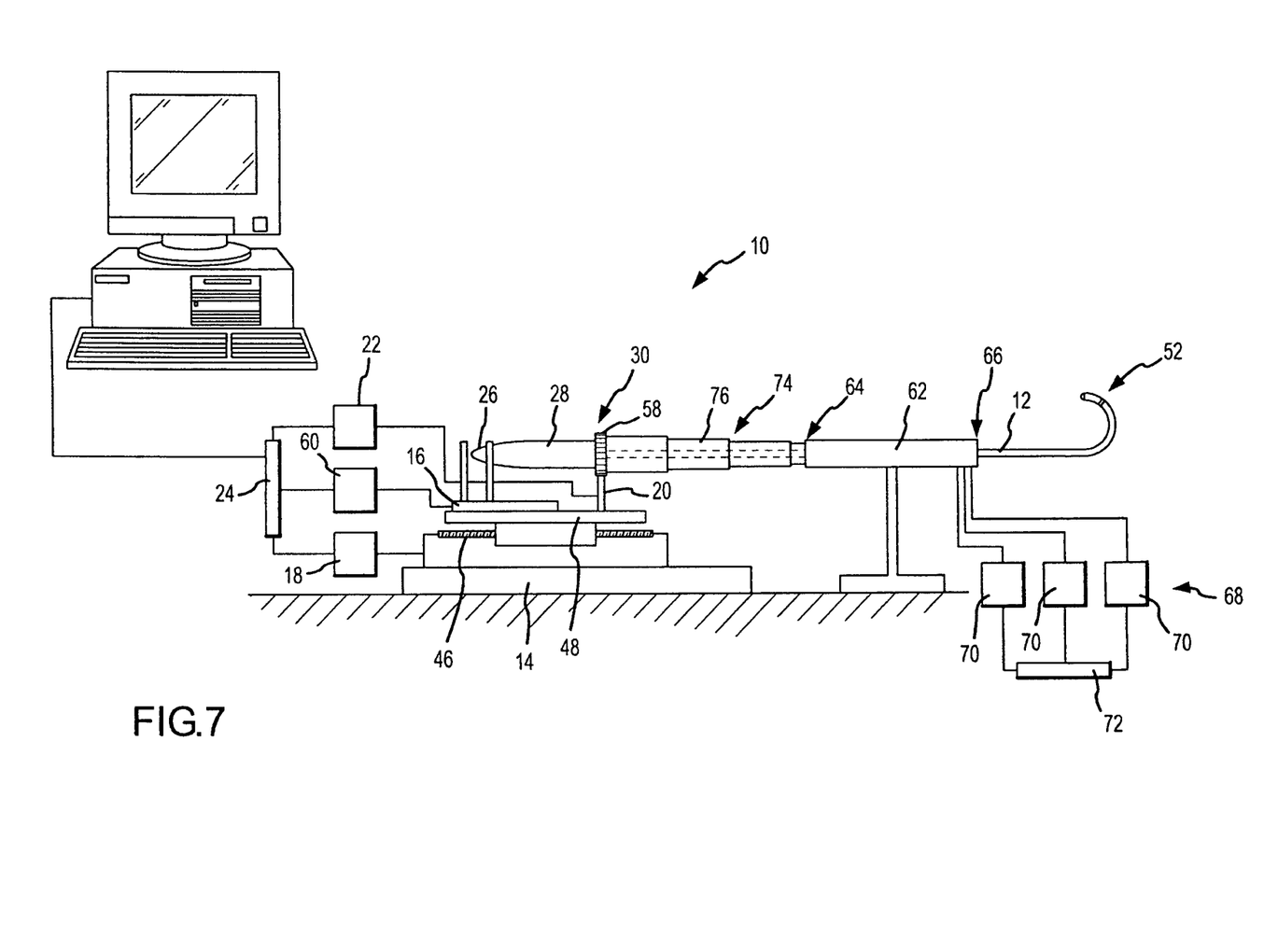
FIG. 7 depicts automatic control of the robotic surgical system according to a predetermined program.
Figure 8:
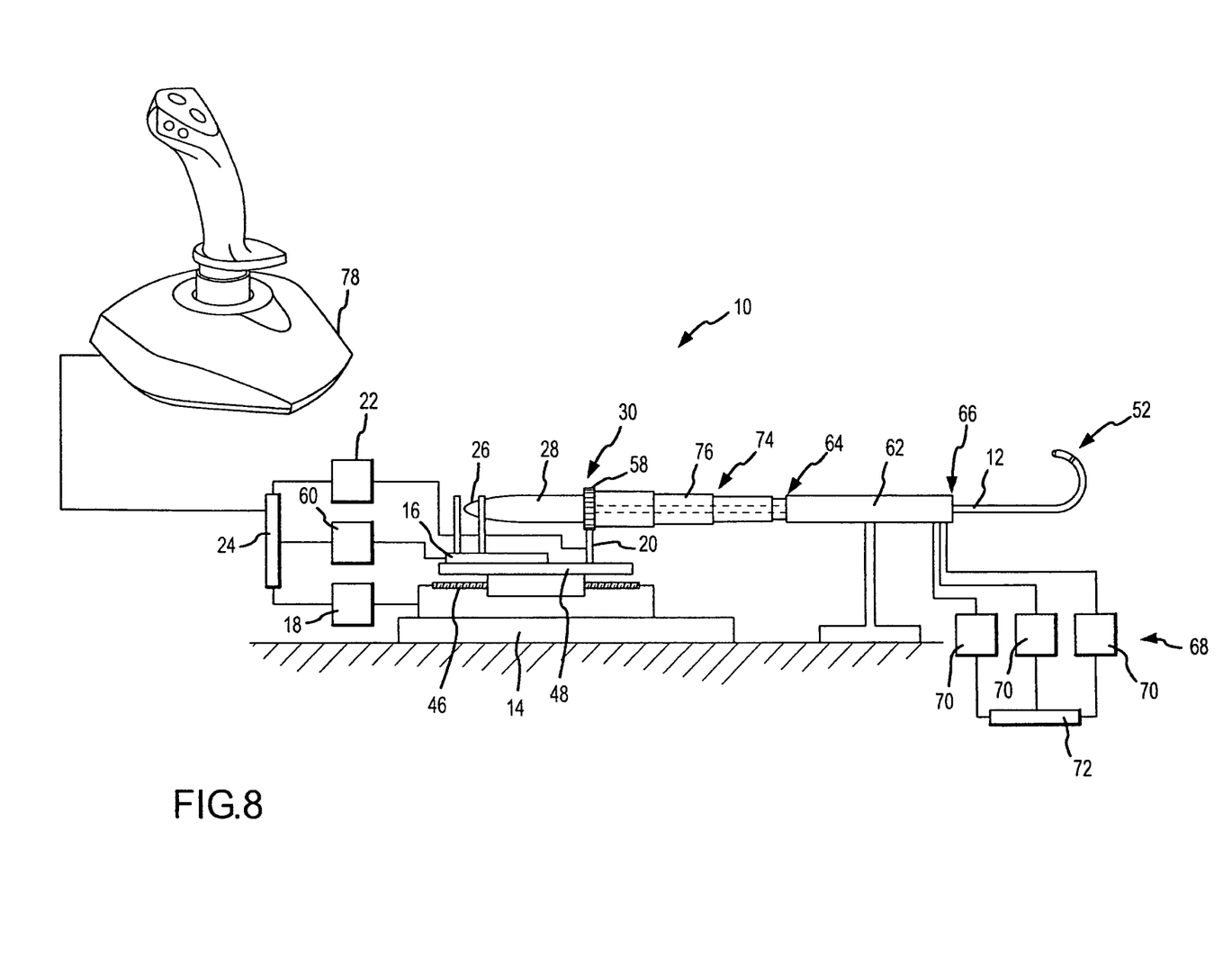
FIG. 8 depicts a user manually controlling the robotic surgical system via an input device.

As depicted in FIGS. 7 and 8, robotic surgical system 10 may be employed to robotically navigate catheter 12 into and through the patient and to one or more sites, which may be target sites, within the patient's body by actuating one or more of translation servo mechanism 18, deflection servo mechanism 22, and rotation servo mechanism 60 (if present) via controller 24. Robotic surgical system 10 may operate automatically according to a computerized program as executed by controller 24 (FIG. 7). It is also contemplated that the user, who may be a surgeon, cardiologist, or other physician, may control robotic surgical system 10 through an appropriate set of controls 78, such as a three-dimensional joystick (e.g., a joystick with three input axes), a steering yoke, or another suitable input device or collection of such devices permitting the user to robotically steer catheter 12 (FIG. 8).

Figure 9:
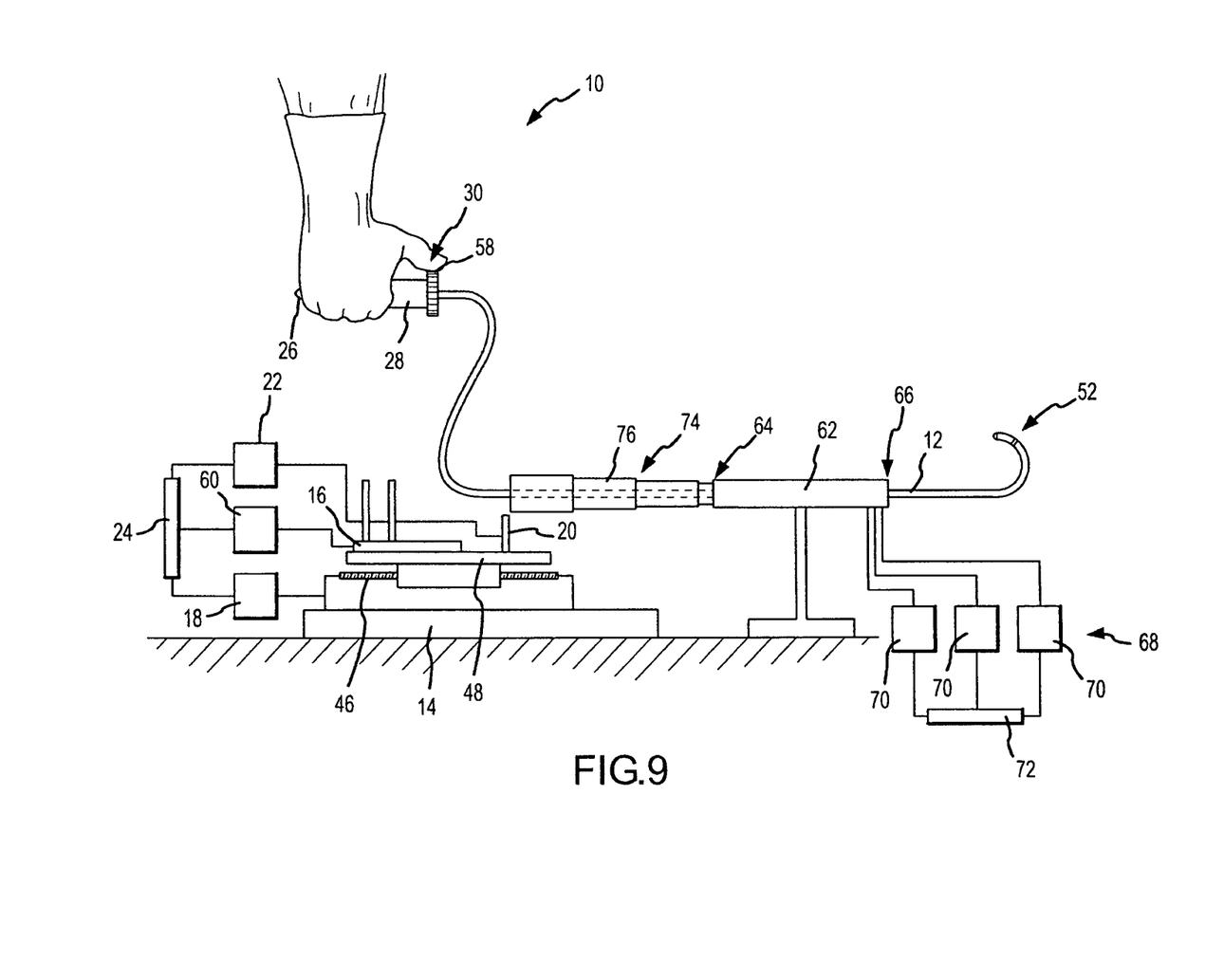
FIG. 9 depicts the user of FIG. 8 manually controlling the steerable catheter after having removed it from the robotic surgical system.

As described above, catheter 12 can be quickly and easily disconnected from catheter holding device 16. Thus, if the user desires to manually control catheter 12 at any point during the procedure, the user may disconnect catheter 12 from the catheter holding device 16 as described above. The user may navigate catheter 12 manually for as long as desired, and then replace it into catheter holding device 16 and resume robotic control. FIG. 9 illustrates the user manually operating catheter 12 after having removed it from catheter holding device 16.

In some embodiments of the invention, multiple robotic surgical systems controlling multiple medical devices may be employed during a procedure. For example, a first robotic surgical system may control an ultrasonic imaging transducer, while a second robotic surgical system may control an ablation catheter. A single controller, or multiple cooperating controllers, may coordinate the multiple medical devices and the multiple robotic surgical systems, for example in conjunction with a single localization system, or alternatively by utilizing data from the ultrasonic imaging transducer to control the movement of the ablation catheter.

Robotic surgical system 10 facilitates precise and accurate navigation of medical device 12 within the patient's body. In addition, since medical device 12 is manipulated primarily robotically, the physician will experience considerably less fatigue during the surgical procedure. Furthermore, robotic control permits a substantially increased degree of complexity in the control and actuation mechanisms that may be incorporated into medical device 12 over those that may be used in a medical device 12 intended solely for human control, enabling an increase in the versatility of medical device 12.

It is also contemplated that the user operating robotic surgical system 10 may be remote from robotic surgical system 10. For example, an expert physician in one city may control robotic surgical system 10 located in a second city via a computer network, such as the Internet.

Although several embodiments of this invention have been described above with a certain degree of particularity, those skilled in the art could make numerous alterations to the disclosed embodiments without departing from the spirit or scope of this invention. For example, the robotic surgical system 10 may be modified to incorporate additional servo mechanisms and controllers operating on additional degrees of freedom.

In addition, one of ordinary skill in the art will appreciate that, though the devices and methods disclosed herein have been described in connection with the treatment of atrial fibrillation, and in particular in connection with the creation of lesions of ablated tissue, they may be used to administer other therapies or to perform other diagnostic procedures.

Further, the devices and methods disclosed herein are capable of use both epicardially and endocardially.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A robotic surgical system, comprising:
a track;
a catheter holding device translatably associated with said track, said catheter holding device including a catheter receiving portion, wherein said catheter receiving portion comprises a rotatable catheter receiving portion;
a translation servo mechanism operatively coupled to said catheter holding device and adapted to control translation of said catheter holding device relative to said track;
a catheter deflection control mechanism;
a deflection servo mechanism operatively coupled to said catheter deflection control mechanism and adapted to control said catheter deflection control mechanism;
a rotation servo mechanism operatively coupled to said rotatable catheter receiving portion and adapted to control said rotatable catheter receiving portion; and
a controller operatively coupled to at least one of said translation servo mechanism and said deflection servo mechanism, wherein said controller is adapted to control said at least one of said translation servo mechanism and said deflection servo mechanism,
wherein the catheter receiving portion is configured to receive a catheter comprising a control handle configured for manual operation and including a manually-actuable catheter deflection actuator, and
wherein said controller is operatively coupled to said rotation servo mechanism and said deflection servo mechanism and is adapted to control at least one of said deflection servo mechanism and said rotation servo mechanism to maintain a substantially constant catheter deflection as said catheter receiving portion rotates.

2. The system according to claim 1, wherein said controller controls both of said deflection servo mechanism and said rotation servo mechanism to maintain a substantially constant catheter deflection as said catheter receiving portion rotates.

* * * * *